United States Patent [19]

Mullins

[11] Patent Number: 5,939,717
[45] Date of Patent: Aug. 17, 1999

[54] METHODS AND APPARATUS FOR DETERMINING GAS-OIL RATIO IN A GEOLOGICAL FORMATION THROUGH THE USE OF SPECTROSCOPY

[75] Inventor: Oliver C. Mullins, Ridgefield, Conn.

[73] Assignee: Schlumberger Technology Corporation, Ridgefield, Conn.

[21] Appl. No.: 09/015,812

[22] Filed: Jan. 29, 1998

[51] Int. Cl.⁶ .............................. G01N 21/35; G01N 8/12
[52] U.S. Cl. ................. 250/255; 250/269.1; 250/265; 250/338.1; 250/339.01; 250/339.06; 250/339.12; 250/343; 73/61.48
[58] Field of Search ................................. 250/253, 256, 250/258, 261, 264, 269.1, 265, 343, 338.5, 339.01, 339.06, 339.1, 339.11, 339.12; 73/61.48

[56] References Cited

U.S. PATENT DOCUMENTS

| | | |
|---|---|---|
| 3,743,426 | 7/1973 | Steinberg . |
| 3,780,575 | 12/1973 | Urbanosky . |
| 3,859,851 | 1/1975 | Urbanosky . |
| 4,336,453 | 6/1982 | Imaki et al. . |
| 4,496,840 | 1/1985 | Fabinski et al. . |
| 4,567,366 | 1/1986 | Shinohara . |
| 4,609,821 | 9/1986 | Summers . |
| 4,620,284 | 10/1986 | Schnell . |
| 4,684,805 | 8/1987 | Shu-Ti et al. . |
| 4,771,176 | 9/1988 | Schiefer et al. . |
| 4,800,279 | 1/1989 | Hieftje et al. ......................... 250/339 |
| 4,829,183 | 5/1989 | McClatchie et al. . |
| 4,958,076 | 9/1990 | Bonne et al. ......................... 250/343 |
| 4,994,671 | 2/1991 | Safinya et al. . |
| 5,166,747 | 11/1992 | Schroeder et al. . |
| 5,167,149 | 12/1992 | Mullins . |
| 5,201,220 | 4/1993 | Mullins . |
| 5,266,800 | 11/1993 | Mullins . |
| 5,285,071 | 2/1994 | LaCount . |
| 5,331,156 | 7/1994 | Hines . |
| 5,412,581 | 5/1995 | Tackett . |
| 5,464,982 | 11/1995 | Drucker et al. . |
| 5,510,269 | 4/1996 | Black et al. . |
| 5,689,114 | 11/1997 | Miyazaki et al. . |

OTHER PUBLICATIONS

"Effect of high pressure on the optical detection of gas by index of refraction methods" by Mullins et al., Applied Optics, vol. 33, No. 34, Dec. 1, 1994, pp. 7963–7970.

*Primary Examiner*—Constantine Hannaher
*Assistant Examiner*—Albert Gagliardi
*Attorney, Agent, or Firm*—Keith G.W. Smith; David P. Gordon

[57] ABSTRACT

Methods according to the invention include providing an OFA tool which subjects formation fluids to NIR illumination and which provides a spectral measurement of peaks at about 6,000 $cm^{-1}$ and about 5,800 $cm^{-1}$. The methods according to the invention also include calculating a ratio of the amplitudes of the absorption peaks to determine GOR. According to an alternate embodiment, the methods of calculating the ratio include referring to a database of spectra of hydrocarbons found in formation fluid and adjusting the amplitudes of the methane and oil peaks to account for the influences of other hydrocarbons on the spectrum of the formation fluid. A borehole apparatus for measuring the spectral peaks of oil and methane includes a testing region, a conduit for directing formation fluid into the testing region, a light source emitting at least near infrared rays into the testing region, a spectral detector optically coupled to the testing region, and a processor coupled to the spectral detector. The testing region is a transparent tube or chamber which is located between the light source and the spectral detector such that light directed from the light source to the spectral detector is interrupted by formation fluid. The spectral detector is preferably a filter spectrograph which measures the spectrum of the light which has been transmitted through the formation fluid in the testing region.

14 Claims, 8 Drawing Sheets

METHODS AND APPARATUS FOR DETERMINING GAS-OIL RATIO IN A GEOLOGICAL FORMATION THROUGH THE USE OF SPECTROSCOPY

The present invention is related to co-owned U.S. Pat. Nos. 4,994,671 to Safinya et al., No. 5,167,149 to Mullins et al., 5,201,220 to Mullins et al., No. 5,266,800 to Mullins et al., and No. 5,331,156 to Hines et al., all of which are hereby incorporated by reference herein in their entireties.

This application is also related to co-owned, application Ser. No. 08/827,647, filed Apr. 10, 1997 now U.S. Pat. No. 5,859,430.

BACKGROUND OF THE INVENTION

1. Field of the Invention

The present invention relates to the analysis of downhole borehole fluids. More particularly, the present invention relates to apparatus and methods for the in situ determination of gas-oil ratio of fluids in a geological formation.

2. State of the Art

Those skilled in the art will appreciate that the ability to conduct an analysis of formation fluids downhole (in situ) is extremely desirable. With that in mind, the assignee of this application has provided a commercially successful borehole tool, the MDT (a trademark of Schlumberger) which extracts and analyzes a flow stream of fluid from a formation in a manner substantially as set forth in co-owned U.S. Pat. Nos. 3,859,851 and 3,780,575 to Urbanosky which are hereby incorporated by reference herein in their entireties. The OFA (a trademark of Schlumberger), which is a module of the MDT, determines the identity of the fluids in the MDT flow stream and quantifies the oil and water content based on the previously incorporated related patents. In particular, previously incorporated U.S. Pat. No. 4,994,671 to Safinya et al. provides a borehole apparatus which includes a testing chamber, means for directing a sample of fluid into the chamber, a light source preferably emitting near infrared rays and visible light, a spectral detector, a data base means, and a processing means. Fluids drawn from the formation into the testing chamber are analyzed by directing the light at the fluids, detecting the spectrum of the transmitted and/or backscattered light, and processing the information accordingly (and preferably based on the information in the data base relating to different spectra), in order to quantify the amount of water and oil in the fluid. As set forth in previously incorporated U.S. Pat. No. 5,266,800 to Mullins, by monitoring optical absorption spectrum of the fluid samples obtained over time, a determination can be made as to when a formation oil is being obtained as opposed to a mud filtrate. Thus, the formation oil can be properly analyzed and quantified by type. Further, as set forth in the previously incorporated U.S. Pat. No. 5,331,156 to Hines et al., by making optical density measurements of the fluid stream at certain predetermined energies, oil and water fractions of a two-phase fluid stream may be quantified.

While the Safinya et al., Mullins, and Hines et al. patents represent great advances in downhole fluid analysis, and are particularly useful in the analysis of oils and water present in the formation, they do not address in detail the gases which may be plentiful in the formation. The issue of in situ gas quantification is addressed in the previously incorporated U.S. Pat. Nos. 5,167,149 to Mullins et al., and 5,201,220 to Mullins et al., and in O. C. Mullins et al., "Effects of high pressure on the optical detection of gas by index-of-refraction methods", *Applied Optics*, Vol. 33, No. 34, pp. 7963–7970 (Dec. 1, 1994) which is also incorporated by reference herein in its entirety, where a rough estimate of the quantity of gas present in the flow stream can be obtained by providing a gas detection module having a detector array which detects light rays having certain angles of incidence. While rough estimates of gas quantities are helpful, it will be appreciated that more accurate measurements are often necessary.

One particularly important measurement for newly discovered oil is the gas-oil ratio (GOR). The GOR is conventionally defined as the volume of gas at STP (standard temperature and pressure) in cubic feet divided by the number of stock tank barrels of oil in a quantity of formation fluid. A GOR of 6,000 $ft^3$/bbl represents approximately equal mass fractional amounts of gas and oil. The GOR must be known in order to establish the size and type of production facilities required for processing the newly discovered oil. For example, a very large GOR of approximately 11,000 $ft^3$/bbl will require the construction of expensive gas handling facilities. It is therefore important to make an accurate measurement of GOR in newly discovered oil so that the appropriate financial investment in production facilities is made.

Currently, the most accurate and preferred method of establishing GOR is to take several samples of formation fluid and subject the samples to laboratory analysis. It is understood that the samples taken must be an accurate statistical representation of the formation fluid in order for the analysis to provide accurate results. In order to enhance the accuracy of the laboratory analysis, many samples are taken from different locations in the formation. However, sample collection of high GOR fluids can be very difficult as samples are not valid if phase separation occurs during sampling. Furthermore, in the process of shipping gas containing samples and performing laboratory analysis, gas can leak from the containers and ruin the samples.

Recently, downhole fluid analysis has been used, providing rough estimates of GOR, in order to aid in the selection of samples for laboratory testing. Theoretically, if estimates of GOR at several locations in the formation are the same or similar, a single fluid sample may be sufficient to provide an accurate laboratory analysis of GOR. One of the recently used methods for estimating GOR relies primarily on the coloration of the fluid sample. Lighter color oils tend to have high gas fractions, generally, although not necessarily indicating a larger GOR. Moreover, this method is indirect and prone to error because the coloration measures the heavy aromatic content whereas, for GOR, one actually wants to measure the methane and light hydrocarbon fractions.

Co-owned U.S. Pat. No. 4,994,671 discloses an apparatus and method for analyzing the composition of formation fluids through the use of spectroscopy. Spectroscopy has been used downhole for distinguishing between oil and water (in the near infrared spectrum), and for distinguishing among oils (in the visible spectrum). However, for several reasons, downhole spectroscopy has not been suggested for distinguishing between gas and oil or for distinguishing among different hydrocarbon gases such as methane ($CH_4$), ethane (having methyl components ($CH_3$)), and higher hydrocarbons which contain predominantly methylene ($CH_2$). First, because the density of a gas is a function of pressure, and because downhole pressures can vary by a factor of thirty or more, the dynamic range of the gas densities likely to be encountered downhole is extremely large. As a result, it is believed that the dynamic range of the spectral absorption at frequencies of interest is also extremely large such as to make a measurement unfeasible;

i.e., the sensitivity of the downhole spectroscopy equipment is typically incapable of handling the large dynamic ranges that are expected to be encountered. Second, due to fact that the condensed phase of hydrocarbon (oil) has a much higher density at downhole pressures than the gas phase, it is believed that a thin film of liquid oil on the OFA window can yield significant absorption. Thus, where an oil film was present, interpretation of the results would yield a determination of a rich gas mixture, where no or little amount of hydrocarbon gas was actually present. Third, the type of spectral analysis typically done uphole to distinguish among hydrocarbon gases cannot be done downhole. In particular, in uphole applications, individual gas constituents are detected by modulating a narrow band source on and off of mid-infrared absorption lines of the gas, where a resulting oscillation in absorption at each modulation frequency would indicate a positive detection of a particular gas. However, at the high pressures encountered downhole, not only are the narrow gas absorption spectral lines merged, but mid-infrared spectroscopy is hindered by the extreme magnitude of the absorption features. Fourth, spectrometers are typically sensitive to changes in temperature, and elevated temperatures encountered downhole can induce spectral changes of the gas sample, thereby complicating any data base utilized.

Co-owned application Ser. No. 08/827,647 now U.S. Pat. No. 5,859,430 discloses a method and apparatus for the downhole compositional analysis of formation gases which utilizes a flow diverter and spectrographic analysis. More particularly, the apparatus includes diverter means for diverting formation gas into a separate stream, and a separate gas analysis module for analyzing the formation gas in that stream. By providing a diverter means and a separate gas analysis module, the likelihood of a having a thin film of oil on the cell window is decreased substantially, thereby improving analysis results. Also, by providing one or more cells with different path lengths, issues of dynamic range are obviated, because where the pressure is higher, light will not be fully absorbed in the cell having a short path length, whereas where the pressure is lower, there will be some absorption in the cell having the longer path length. The methods and apparatus of the '647 application are useful in determining what types of gas are present in the formation fluid, but are not particularly useful in determining GOR.

SUMMARY OF THE INVENTION

It is therefore an object of the invention to provide methods and apparatus for determining gas-oil ratio in formation fluids.

It is also an object of the invention to provide methods and apparatus for the in situ determination of the gas-oil ratio of formation fluids.

It is another object of the invention to provide methods and apparatus for the downhole spectroscopic determination of gas-oil ratio of formation fluids.

It is a further object of the invention to provide methods and apparatus for the downhole determination gas-oil ratio in formation fluids, which methods and apparatus remain relatively accurate in high temperature and high pressure environments.

In accord with these objects which will be discussed in detail below, the methods and apparatus of the present invention arise from several discoveries about the nature of a supercritical gas-oil mixture, i.e. a mixture of methane ($CH_4$) molecularly dispersed in oil ($CH_2$) at high temperature and pressure, also known as "live crude oil". In particular, it was discovered that the NIR (near infrared) absorption spectrum of such a single phase or supercritical mixture is equal to the sum of the NIR absorption spectra for the oil component and the methane component. In other words, the spectral position of methane dissolved in crude oil is the same as methane gas. In addition, it was discovered that the effects of high temperature and pressure on the spectrum of methane are less significant with regard to peak positions than with regard to peak intensities. In particular, it was observed that the characteristic absorption peak at about wavenumber 6,000 $cm^{-1}$ (wavelength 1.667 microns) of methane remained relatively constant through temperatures over 200° C. and pressures over 20,000 psi. In addition, the characteristic absorption peak at about wavenumber 5,800 $cm^{-1}$ (wavelength 1.720 microns) of crude oil remained relatively constant through the same temperatures and pressures. Most significantly, it was discovered that the absorption peak area of methane is linearly related to the density of gas and that this relationship holds true over a very large range of densities.

Therefore, methods according to the invention include providing an OFA-type tool which subjects formation fluids to NIR illumination and which provides a spectral measurement of peaks at and/or around about 6,000 $cm^{-1}$ and about 5,800 $cm^{-1}$ (the absorption peaks of methane and crude oil respectively). The methods according to the invention also include calculating a ratio of the amplitudes of the absorption peaks to determine GOR. According to an alternate embodiment of the invention, the methods of calculating the gas-oil ratio include referring to a database of spectra of hydrocarbons found in formation fluid and adjusting the amplitudes of the methane and oil peaks to account for the influences of other hydrocarbons on the spectrum of the formation fluid.

According to the invention, a borehole apparatus for measuring the spectral peaks of oil and methane includes a testing region, a conduit for directing formation fluid into the testing region, a light source emitting at least near infrared rays into the testing region, a spectral detector optically coupled to the testing region, and a processor coupled to the spectral detector. The testing region is a transparent tube or chamber which is located between the light source and the spectral detector such that light directed from the light source to the spectral detector is interrupted by formation fluid. The spectral detector is preferably a spectrometer which measures the spectrum of the light which has been transmitted through the formation fluid in the testing region. The processor is preferably a microprocessor and is also preferably provided with a database of information about the spectra of different hydrocarbons found in formation fluids.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
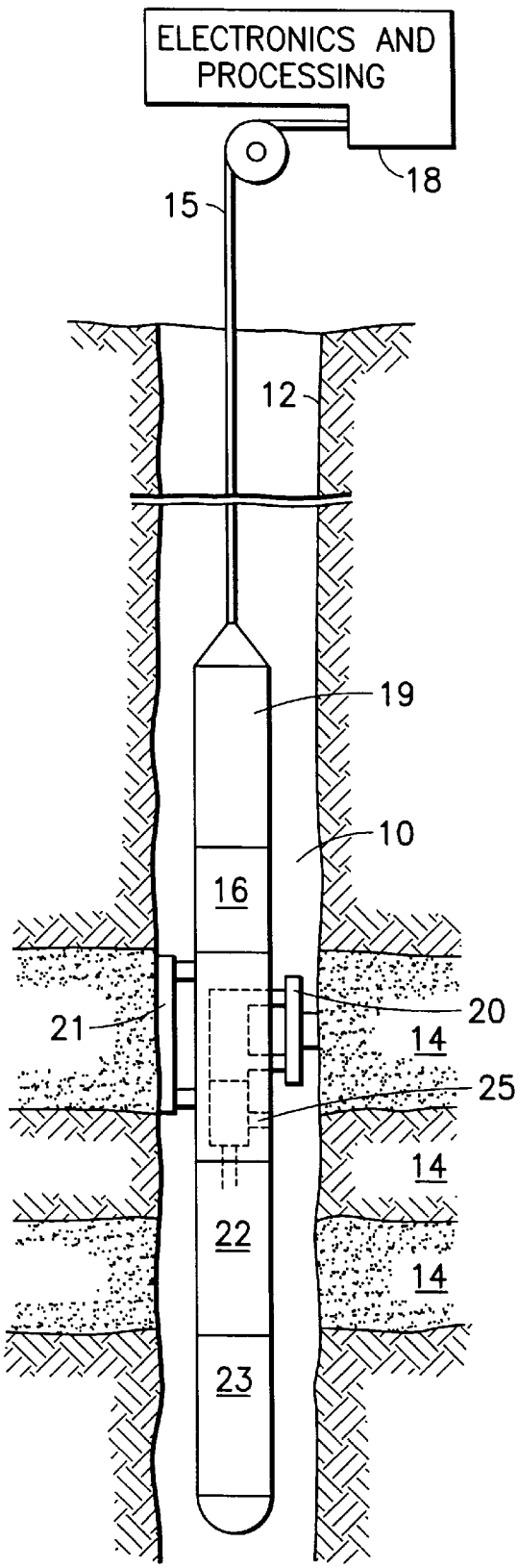
FIG. 1 is a schematic diagram of a borehole apparatus for analyzing formation fluids.

Referring now to FIG. 1, a borehole tool 10 for analyzing fluids from the formation 14 is suspended in the borehole 12 from the lower end of a typical multiconductor cable 15 that is spooled in a usual fashion on a suitable winch (not shown) on the formation surface. On the surface, the cable 15 is preferably electrically coupled to an electrical control system 18. The tool 10 includes an elongated body 19 which encloses the downhole portion of the tool control system 16. The elongated body 19 also carries a selectively extendable fluid admitting assembly 20 and a selectively extendable tool anchoring member 21 which are respectively arranged on opposite sides of the body. The fluid admitting assembly 20 is equipped for selectively sealing off or isolating selected portions of the wall of the borehole 12 such that pressure or fluid communication with the adjacent earth formation is established. Also included with tool 10 are a fluid analysis module 25 through which the obtained fluid flows. The fluid may thereafter be expelled through a port (not shown) or it may be sent to one or more fluid collecting chambers 22 and 23 which may receive and retain the fluids obtained from the formation. Control of the fluid admitting assembly, the fluid analysis section, and the flow path to the collecting chambers is maintained by the electrical control systems 16 and 18.

Additional details of methods and apparatus for obtaining formation fluid samples may be had by reference to U.S. Pat. Nos. 3,859,851 and 3,780,575 to Urbanosky, and U.S. Pat. No. 4,994,671 to Safinya et al. which are hereby incorporated by reference herein. It should be appreciated, however, that it is not intended that the invention be limited to any particular method or apparatus for obtaining the formation fluids.

Figure 2:
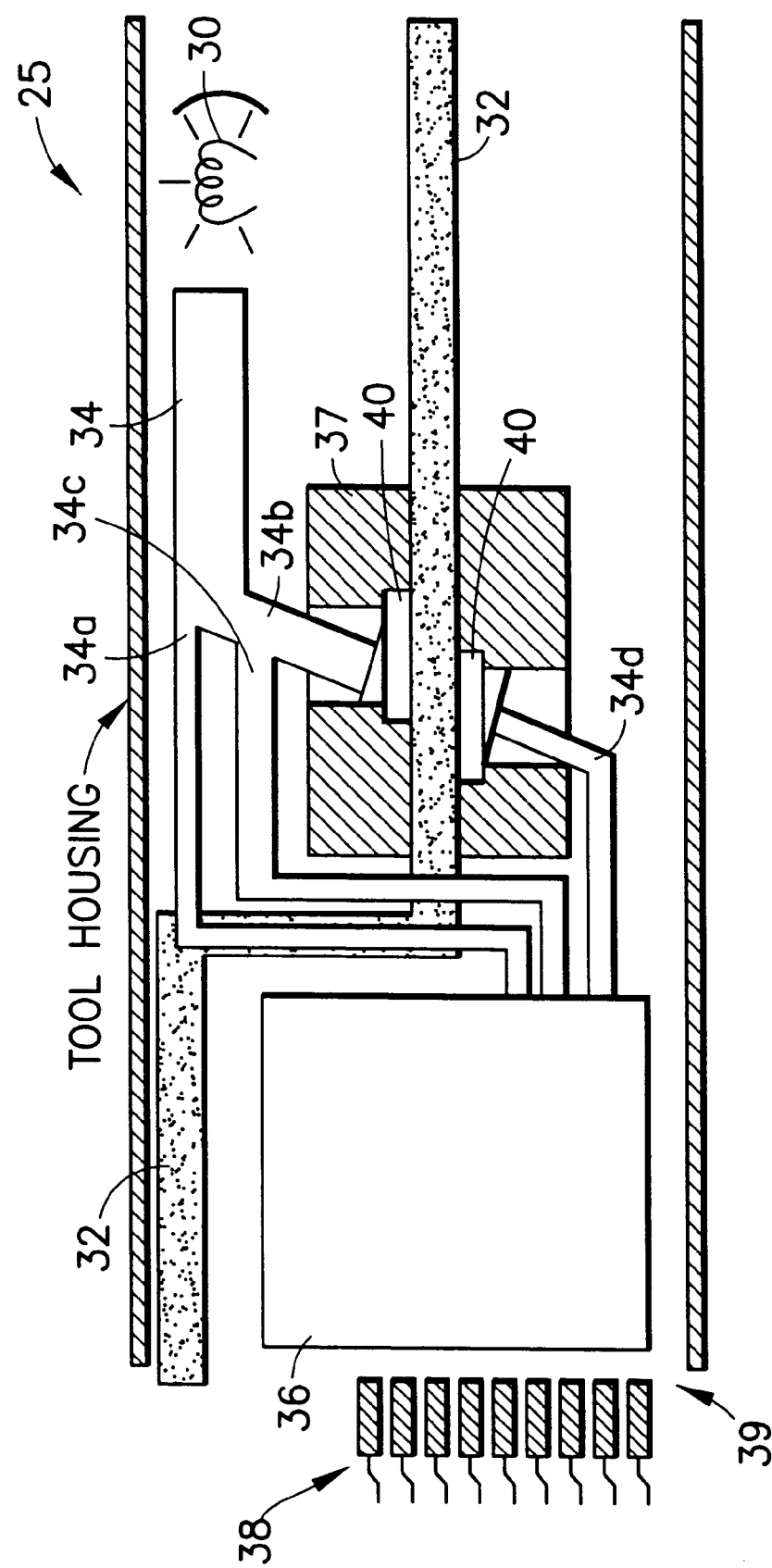
FIG. 2 is a schematic diagram of the preferred near infrared fluid analysis module of FIG. 1.

Turning now to FIG. 2, a preferred fluid analysis module 25 includes a light source 30, a fluid sample tube 32, optical fibers 34, and a filter spectrograph 39 which includes a fiber coupler or distributor 36 and an associated detector array 38. The light source 30 is preferably an incandescent tungsten-halogen lamp which is kept at near atmospheric pressure. The light source 30 is relatively bright throughout the near infrared wavelength region of 1 to 2.5 microns and down to approximately 0.5 microns, and has acceptable emissions from 0.35 to 0.5 microns. Light rays from the light source 30 are preferably transported from the source to the fluid sample by at least part of a fiber optic bundle 34. The fiber optic bundle 34 is preferably split into various sections. A first small section 34a goes directly from the light source 30 to the distributor 36 and is used to sample the light source. A second section 34b is directed into an optical cell 37 through which the sample tube 32 runs and is used to illuminate the fluid sample. A third bundle 34d collects light transmitted or scattered through the fluid sample and provides the filter spectrograph with the light for determining the absorption spectrum of the fluid sample. Optionally, though not necessarily preferred, a fourth fiber optic bundle 34c collects light substantially backscattered from the sample for spectrographic analysis. The backscattered spectrum may be useful if multiple phases are present simultaneously. Preferably, however, this determination is made with a separate gas detector as described in previously incorporated U.S. Pat. No. 5,167,149. A three position solenoid (not shown) is used to select which fiber optic bundle is directed toward the filter spectrograph 39. Preferably, a light chopper (not shown) modulates the light directed at the spectrograph at 500 Hz to avoid low frequency noise in the detectors.

As mentioned above, optical bundle 34b directs the light towards the fluid sample. The fluid sample is obtained from the formation by the fluid admitting assembly and is sent to the fluid analysis section 25 in tube 32. The sample tube 32 is preferably a two by six millimeter rectangular channel which includes a section 40 with windows made of sapphire. This window section 40 is located in the optical cell 37 where the light rays are arranged to illuminate the sample. Sapphire is chosen for the windows because it is substantially transparent to the spectrum of the preferred light source. and because it is highly resistant to abrasion. As indicated schematically in FIG. 2, the window areas 40 may be relatively thick compared to the rest of the tube 32 to withstand high internal pressure. The fiber optic bundles 32b and 32d are preferably not perpendicular to the window areas 40 so as to avoid specular reflection. The window areas are slightly offset as shown in FIG. 2 to keep them centered in the path of the transmitted light. The signals from the detectors are digitized, multiplexed, and transmitted uphole via the cable 15 to the processing electronics 18 shown in FIG. 1.

Those skilled in the art will appreciate that each element in the detector array 38 is provided with a band pass filter for a particular wavelength band. According to a presently preferred embodiment, the detector array has ten elements which detect light at or about the following wavenumbers: 21000 $cm^{-1}$, 18600 $cm^{-1}$, 15450 $cm^{-1}$, 9350 $cm^{-1}$, 7750 $cm^{-1}$, 6920 $cm^{-1}$, 6250 $cm^{-1}$, 6000 $cm^{-1}$, 5800 $cm^{-1}$, and 5180 $cm^{-1}$. It will be appreciated that the first three wavenumbers represent visible blue, green, and red light and are preferably used to perform the type of analysis described in previously incorporated U.S. Pat. No. 5,266,800. The remaining wavenumbers are in the NIR spectrum and are used to perform analyses as described herein.

As previously indicated, the detector array elements determine the intensity of the light passing through the fluid in the tube 32 at the ten different wavebands. For purposes of the present invention, however, it is only necessary that there be two detectors, one which detects light around wavenumber 5800 $cm^{-1}$ and another which detects light around wavenumber 6000 $cm^{-1}$. Preferably, one or two detectors are provided which measure a baseline intensity, i.e. the intensity of a wavelength of light which is not absorbed by formation fluid, e.g. the detector at 9350 $cm^{-1}$ which is not absorbed by any formation fluid or 6920 $cm^{-1}$ which is not absorbed by hydrocarbons but is absorbed by water. The optical density of the fluid at particular wavelengths is determined according to Equation 1.

$$OD(\lambda) = \log\frac{I(\text{source})}{I(\lambda)} \quad (1)$$

Thus, if the intensity at wavelength $\lambda$ is equal to the intensity of the source, there is no absorption, and the fraction in Equation 1 will be equal to 1 while the $OD(\lambda)$ will equal 0. If the intensity at wavelength $\lambda$ is one tenth the intensity of the source, the fraction in Equation 1 will be equal to 10 and the OD(λ) will equal 1. It will be appreciated that as the intensity at λ decreases, the optical density OD(λ) will increase.

As mentioned above, the intensity of the source is preferably measured by measuring the light passing through the sample at a wavelength where no absorption occurs. This compensates for any light loss due to backscattering and provides a more accurate measure of optical density.

Figure 3:
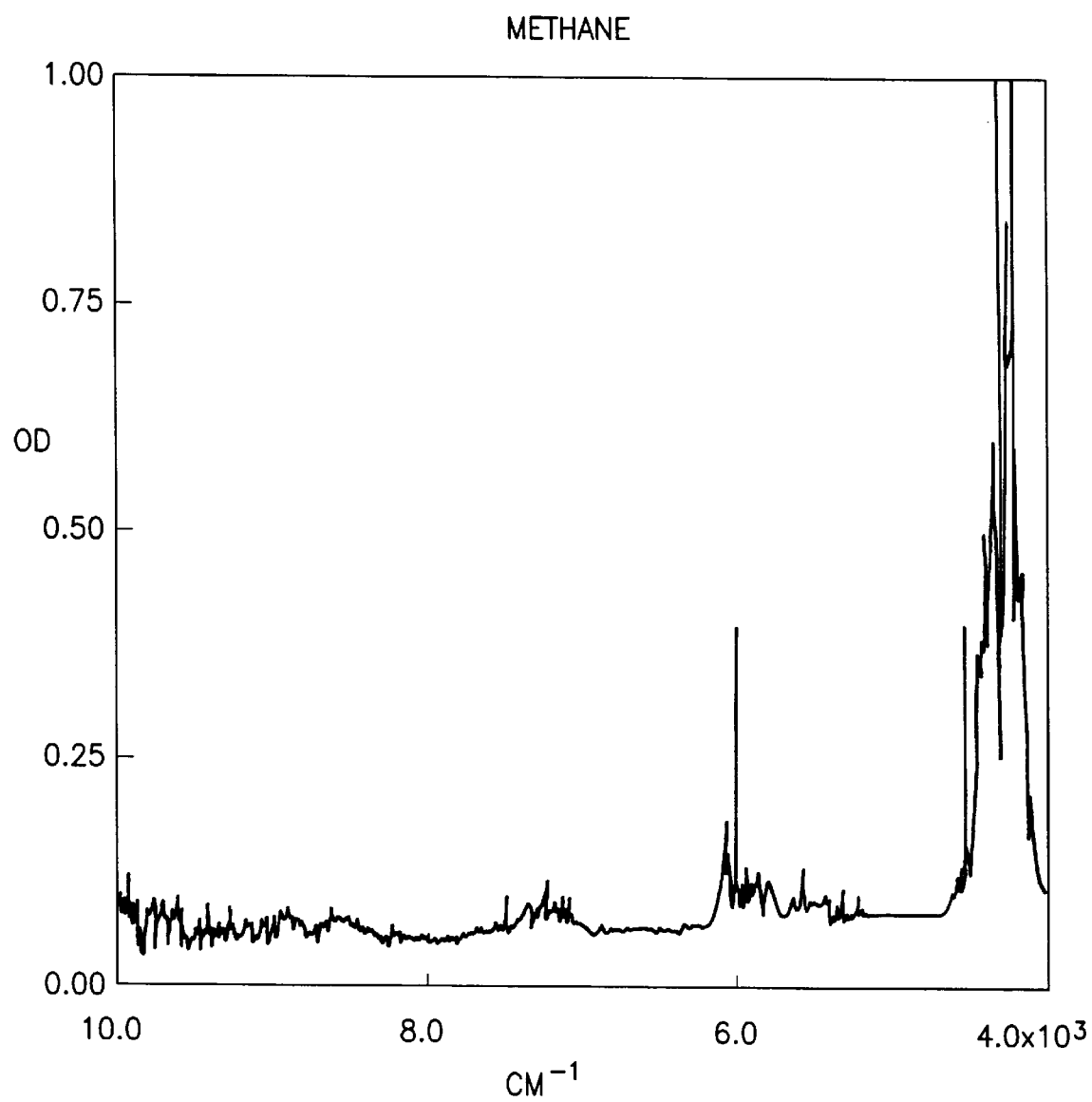
FIG. 3 is a graph of the NIR absorption spectrum of methane at low pressure and low temperature.
Figure 4:
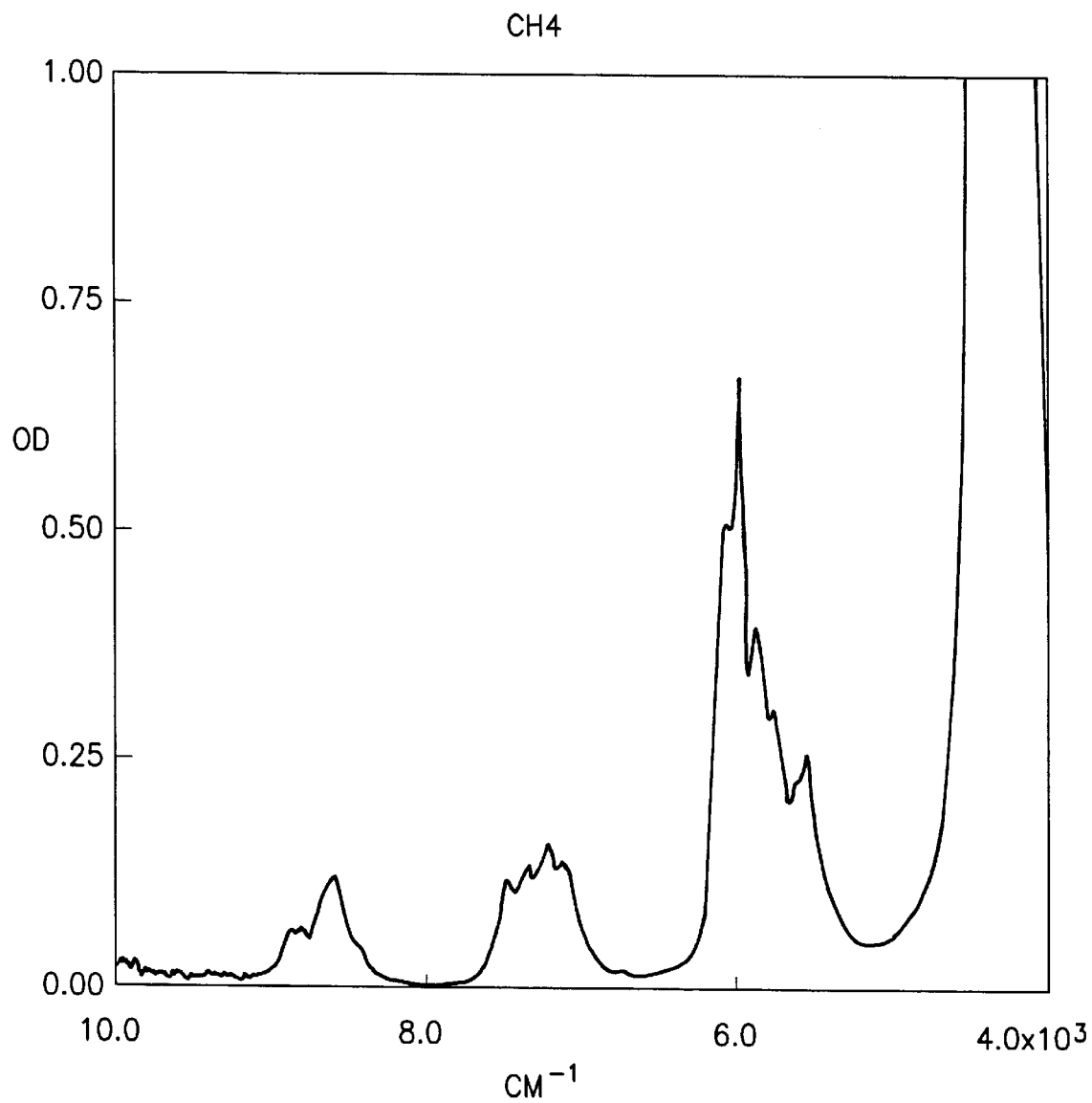
FIG. 4 is a graph of the NIR absorption spectrum of methane at high pressure and high temperature.

As mentioned above, the methods of the invention include measuring the absorption spectra of formation fluid at wavenumbers in the vicinity of $6.0 \times 10^3$ cm$^{-1}$ and $5.8 \times 10^3$ cm$^{-1}$. It has been discovered by the inventor that absorption at these wavenumbers is indicative of the presence of methane and oil, respectively, even at the extremely high temperatures and pressures encountered downhole in the formation. For example, with reference to FIG. 3, the NIR absorption spectrum for methane at room temperature and low pressure exhibits a characteristic peak optical density at $6.0 \times 10^3$ cm$^{-1}$. This characteristic peak is also exhibited by methane under high pressure and temperature as seen in FIG. 4 which shows the NIR absorption spectrum for methane at 20,000 psi and 204° C. In FIG. 4, the characteristic peak for methane is still located at $6.0 \times 10^3$ cm$^{-1}$ although the amplitude of the peak is significantly increased. Similar results were discovered for crude oil which exhibited a characteristic absorption peak at $5.8 \times 10^3$ cm$^{-1}$.

Figure 5:
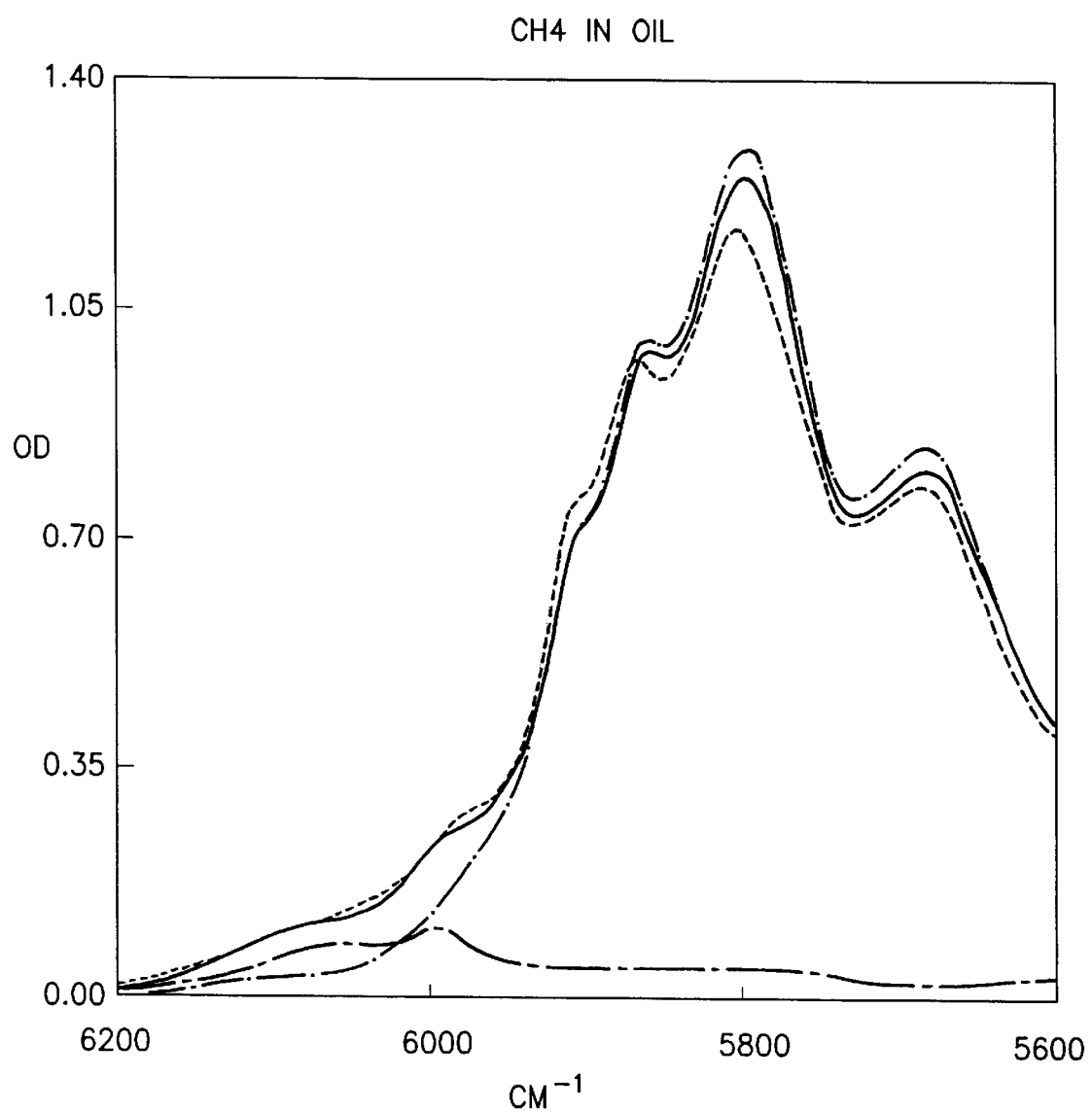
FIG. 5 is a composite graph showing the spectra of crude oil containing no methane, dilute methane gas, the weighted sum of the spectra of oil and methane, and the spectrum of oil containing methane.
Figure 6:
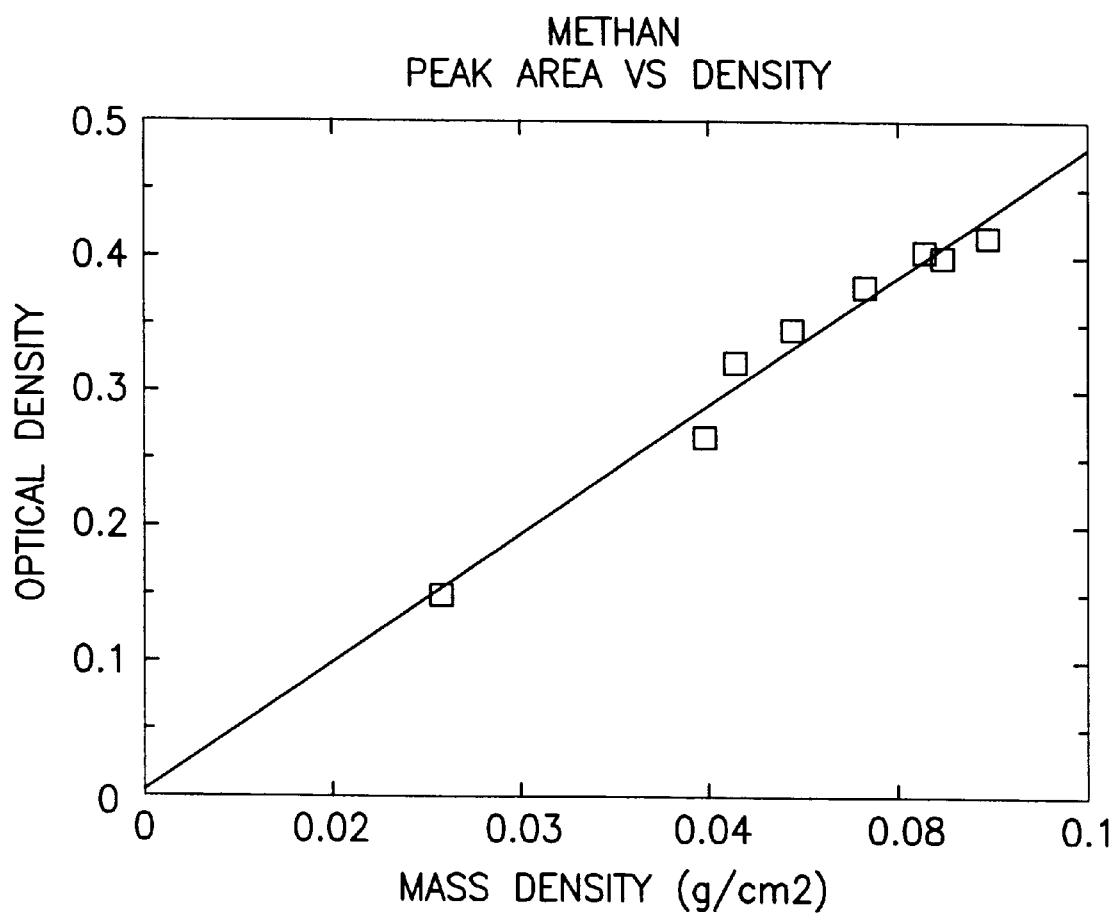
FIG. 6 is a plot of experimental values and a linear function extrapolated from the values.

The inventor also discovered that the absorption spectrum of live oil exhibits an identifiable peak at $6.0 \times 10^3$ cm$^{-1}$ and an identifiable peak at $5.8 \times 10^3$ cm$^{-1}$. More particularly, FIG. 5 illustrates the spectrum of 100% crude oil without methane (shown in chain-dot line), the spectrum of an 8–10% condensed phase density methane without oil (shown in chain-dash line), and the spectrum of a "live oil" mixture of oil with 8–10% methane (shown in dashed line). In addition, FIG. 6 shows that the weighted sum (solid line) of the methane spectrum and the oil spectrum is substantially equal to the spectrum of the live oil (dashed line).

Most significantly, the inventor also discovered that the absorption peak area of methane is linearly related to the density of gas and that this relationship holds true over a very large range of densities. Experiments were conducted using a Mattson Cygnus 100 FTIR spectrometer with a tungsten-iodide light source and a quartz beam splitter. The collimated optical beam from the spectrometer was steered to an optical bench adjacent to a high pressure, high temperature autoclave. The focused optical beam traversed a 3 mm optical cell having two 7 mm thick sapphire windows. The optical cell was located in the autoclave and optical beam, after exiting the autoclave, was focused onto a nitrogen-cooled detector. Several measurements were made of absorption strength in the 5800 cm$^{-1}$ to 6200 cm$^{-1}$ window at different temperatures and pressures of methane. The absorption strength measurements were made by integrating the amplitude of the absorption spectrum on the waveband 5800 cm$^{-1}$ to 6200 cm$^{-1}$. The integrated amplitude provides a more accurate measure of absorption than amplitude by itself. While the effects of temperature and pressure tend to broaden peaks as their amplitude is decreased, the area under the peaks remains an accurate indicator of the absorption strength. The test results are summarized in Table 1 below.

| T (° C.) | P (psi) | OD | Z | ρ (g/cc) |
|---|---|---|---|---|
| 24 | 1,975 | 0.150 | 0.87 | 0.101 |
| 24 | 3,900 | 0.267 | 0.92 | 0.189 |
| 24 | 9,900 | 0.418 | 1.50 | 0.295 |
| 65 | 10,130 | 0.404 | 1.41 | 0.282 |
| 107 | 10,200 | 0.384 | 1.40 | 0.254 |
| 149 | 10,050 | 0.349 | 1.38 | 0.229 |
| 204 | 10,160 | 0.323 | 1.35 | 0.209 |
| 211 | 20,150 | 9.407 | 2.00 | 0.276 |

Table 1 shows the measured optical density OD of methane in the 5800 cm$^{-1}$ to 6200 cm$^{-1}$ window at different temperatures T and pressures P. Table 1 also shows the compressibility factor Z (=PV/RT) for methane for the temperatures and pressures at which measurements were made. Given the temperature T, the pressure P, and the compressibility factor Z, the mass density ρ was computed for each measurement. The measured optical densities and corresponding calculated mass densities were plotted relative to each other as shown in FIG. 6. It should be noted that the mass densities used in the plot of FIG. 6 are one third the values shown in Table 1. This scaling of the mass densities relates to the fact that the length of the chamber in which measurements were made was 3 mm. Scaling the mass densities of Table 1 converts the values to mass per unit area rather than mass per unit volume so that the measurements may be applied to chambers of different lengths. As clearly illustrated in FIG. 6, measured optical densities are linearly related to the calculated mass densities.

The inventor has also considered the issue of absorption per unit density (mass per unit area) of methane (gas) and heptane (oil). The absorption peak intensities for equal volumes of methane and heptane will be different unless the peak intensities are normalized to account for the different absorption strengths. One method of normalizing the peak intensities is to normalize by mass per unit area. Using this method, it is recognized that the integrated peak intensity for methane is 4.69 OD/g/cm$^2$ and the integrated peak intensity for heptane is 3.72 OD/g/cm$^2$. Using these relative absorption per unit density values, the peak intensities can easily be normalized. One could also normalize with absorption per unit mole of $CH_4$ for methane and —$CH_2$— for oil depending on the desired final units. In either case, the peak intensities for methane and heptane are within 25% of each other.

Given the discoveries made regarding the spectra of oil and methane, and the OFA tool described herein with optical windows at 6000 cm$^{-1}$ and 5800 cm$^{-1}$, those skilled in the art will appreciate that the absorption spectra of oil and methane can be used to determine the GOR of fluid samples deep in a geological formation.

Figure 7:
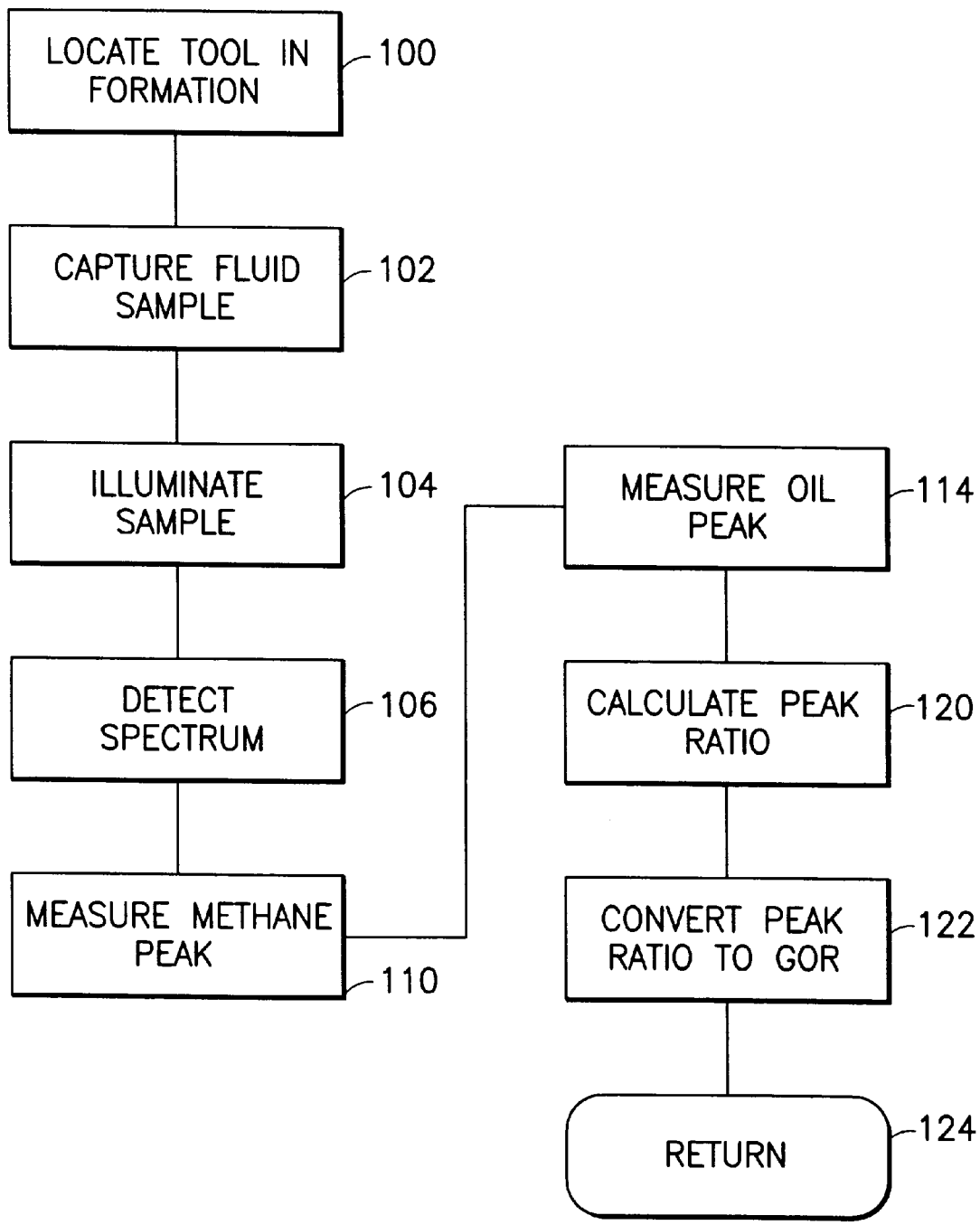
FIG. 7 is a schematic flow chart illustrating one method of the invention.

Turning now to FIG. 7, an exemplary method of the present invention is illustrated in the form of a flow chart. According to the invention as shown at 100 in FIG. 7, the OFA tool is lowered into the borehole of a formation and located at a location for taking a fluid sample. A sample of fluid is captured at 102 and the sample is illuminated at 104. The spectrum of light transmitted through the sample is detected at 106. The methane absorption peak is measured at 110 and the oil absorption peak is measured at 114. The peak ratio is calculated at 120 which may include normalization of the peaks as described above. The (normalized) ratio of the methane absorption peak to the oil absorption peak is directly proportional to the GOR. In fact, the peak to peak ratio is simply converted to GOR at 122 by scaling it by a factor of 6,000, this number being the number of ft$^3$/bbl for a 1:1 ratio of gas to oil. Typically, several samples of downhole fluid will be analyzed. Therefore, as shown in FIG. 7, the method returns a 124 to locating the tool at 100 so that an additional sample may be taken and analyzed as described above.

Figure 8:
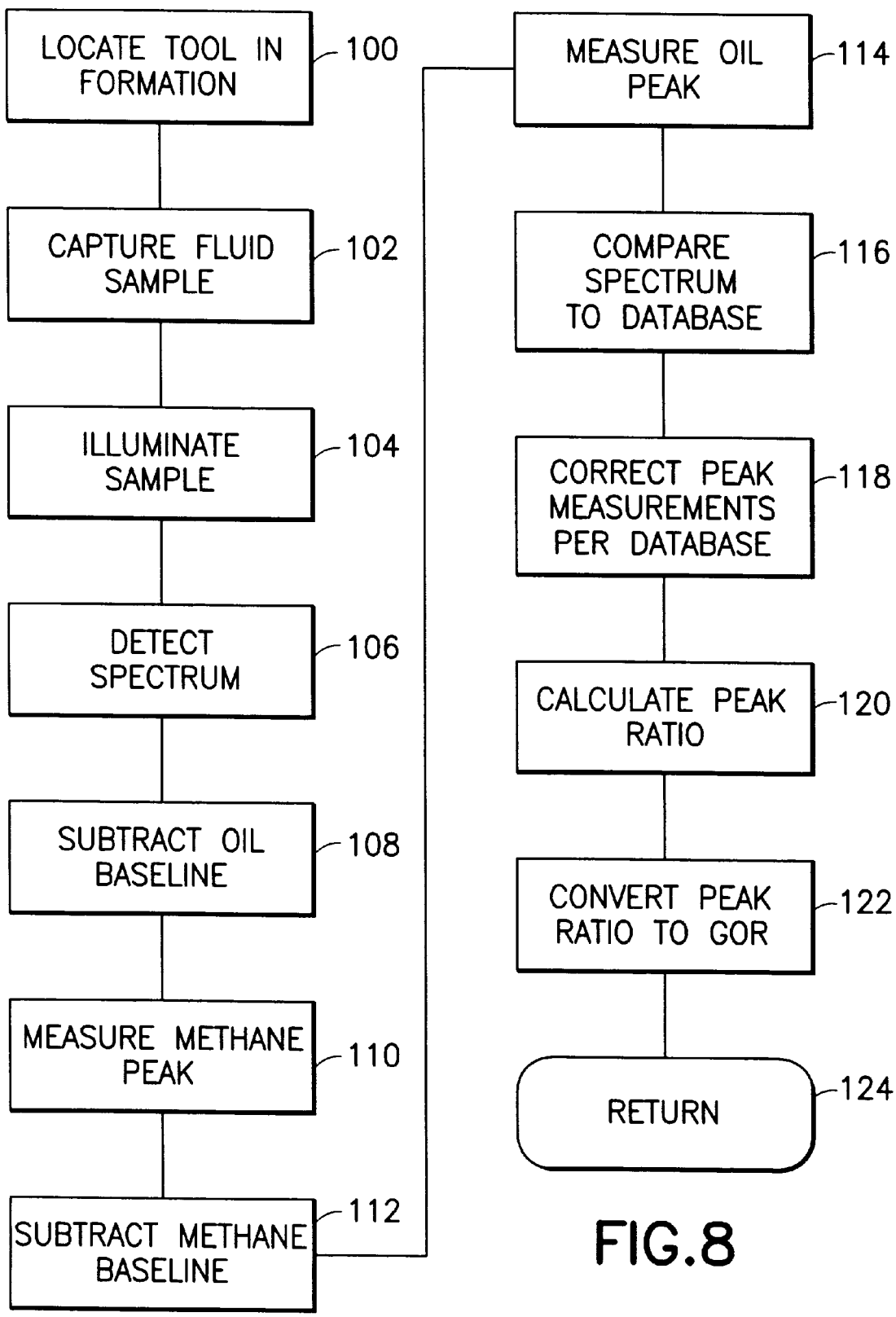
FIG. 8 is a schematic flow chart illustrating another method of the invention.

As mentioned above, additional analyses and manipulation of the spectra may be performed to enhance the accuracy of the GOR determination. Some optional steps are illustrated in the method shown in FIG. 8. As shown in FIG. 8, prior to measuring the methane peak at 110, an oil baseline spectrum is subtracted from the spectrum detected at 106. This may enhance the analysis of the methane peak by removing any oil spectrum influence which might exist. Similarly, before measuring the oil peak at 114, a methane baseline spectrum is subtracted from the spectrum detected at 106. This may enhance the analysis of the oil peak by removing any methane spectrum influence which might exist. It will be appreciated that the baseline subtractions may be performed iteratively. Further, in order to remove any adverse spectral effects of other hydrocarbons which may be present in the formation fluid, the spectrum may be compared at 116 to a database of spectra to account for the presence of other hydrocarbons in the sample which may have influenced the magnitude of the oil and methane peaks. When such a database is used, the peak measurements will be corrected accordingly at 118 prior to calculating a peak ratio at 120.

It will be appreciated that the database correction step(s) discussed above may be performed on the detected spectrum prior to measuring peaks or may be arranged to directly correct the measured peaks. The database may include spectral information for ethane and wet gases which contain a large mass fraction of the methyl group —$CH_3$ to distinguish these absorption spectra from crude oils which contain mostly —$CH_2$—.

Those skilled in the art will appreciate that the disclosed apparatus for detecting the absorption spectrum described herein inherently produces an integrated amplitude. This occurs because the spectral detectors used do not detect at a single wavelength, but detect all light within a waveband which may be relatively narrow or relatively broad depending on the detector and which may be centered around a particular wavelength. Thus, the steps of measuring the absorption peaks described above automatically integrates the absorption peaks over a bandwidth. It will be understood that it is possible to avoid the integration through filtering and still obtain similar results. However, it is believed that allowing integration will provide more accurate results.

There have been described and illustrated herein several embodiments of methods and apparatus for determining gas-oil ratio in a geological formation. While particular embodiments of the invention have been described, it is not intended that the invention be limited thereto, as it is intended that the invention be as broad in scope as the art will allow and that the specification be read likewise. Thus, while particular light source and spectral detector have been disclosed, it will be appreciated that other spectral detectors and light sources could be utilized provided that they perform the same functions as described herein. Also, while a particular borehole apparatus has been shown, it will be recognized that other types of borehole apparatus could be used to make spectral analyses of formation fluids in accord with the concepts of the invention. Moreover, while particular steps have been disclosed in reference to "correcting" the spectrum of downhole fluid, it will be appreciated that other "corrective" steps could be used as well. It will therefore be appreciated by those skilled in the art that yet other modifications could be made to the provided invention without deviating from its spirit and scope as so claimed.

I claim:

1. A method for determining gas-oil ratio in a geological formation, said method comprising:
   a) subjecting in situ formation fluid to NIR illumination;
   b) detecting a spectrum of NIR absorption in the formation fluid;
   c) measuring NIR absorption at a wavelength associated with gas and at a wavelength associated with oil; and
   d) calculating the ratio of the gas NIR absorption to the oil NIR absorption.

2. A method according to claim 1, further comprising:
   e) converting the ratio of the absorption to gas-oil ratio (GOR).

3. A method according to claim 2, wherein:
   said step of converting includes multiplying by a constant.

4. A method according to claim 3, wherein:
   said constant is approximately 6,000.

5. A method according to claim 1, wherein:
   the wavelength associated with gas is approximately 1.6 microns, and the wavelength associated with oil is approximately 1.7 microns.

6. A method according to claim 1, further comprising:
   e) measuring NIR absorption amplitude at a plurality of wavelengths; and
   f) comparing the measurements of NIR absorption amplitude at a plurality of wavelengths to a database.

7. A method according to claim 6, further comprising:
   g) correcting the spectrum of NIR absorption based on the database comparison prior to calculating the ratio.

8. A method for downhole determining gas-oil ratio in a geological formation, said method comprising:
   a) capturing downhole a sample of formation fluid;
   b) subjecting formation fluid to NIR illumination downhole;
   c) detecting NIR absorption in the formation fluid;
   d) integrating NIR absorption amplitude over a waveband associated with gas NIR absorption;
   e) integrating NIR absorption amplitude over a waveband associated with oil NIR absorption; and
   f) calculating the ratio of the integrated absorption amplitudes.

9. A method according to claim 8, further comprising:
   e) converting the ratio of the integrated absorption amplitudes to gas-oil ratio.

10. An apparatus for determining gas-oil ratio of fluid in a geological formation, said apparatus comprising:
    a) a light source having a spectrum which includes NIR;
    b) a spectral detector which detects at least a portion of the NIR spectrum;
    c) a fluid chamber located between said light source and said spectral detector such that light from said light source passes through fluid in said fluid chamber and toward said spectral detector; and
    d) a processor means coupled to said spectral detector for calculating a ratio of NIR absorption associated with gas to NIR absorption associated with oil.

11. An apparatus according to claim 10, wherein:
    said light source, said spectral detector, and said fluid chamber are located in a borehole logging tool.

12. An apparatus according to claim 11, further comprising:

e) a fluid admitting assembly coupled to said fluid chamber and located in said borehole logging tool, wherein said fluid admitting assembly is operable to selectively admit fluid into said fluid chamber.

13. An apparatus according to claim 12, further comprising:
f) a tool anchoring member coupled to said borehole logging tool, wherein said tool anchoring member is operable to selectively fix the location of said logging tool in a borehole.

14. An apparatus according to claim 10, wherein:
said spectral detector detects light having a wavenumber of approximately 6000 cm$^{-1}$ and light having a wavenumber of approximately 5800 cm$^{-1}$.

* * * * *